United States Patent
Wu et al.

(10) Patent No.: US 7,531,194 B2
(45) Date of Patent: May 12, 2009

(54) PLANT EXTRACTS FOR THE TREATMENT OF RHEUMATOID ARTHRITIS

(75) Inventors: Rey-Yuh Wu, Taipei (TW); Jia-Ming Chang, Taipei (TW); Chun-Ming Cheng, Taipei (TW); Yuh-Shan Chung, Taipei (TW)

(73) Assignee: Development Center for Biotechnology, Xizhi (TW)

( * ) Notice: Subject to any disclaimer, the term of this patent is extended or adjusted under 35 U.S.C. 154(b) by 0 days.

(21) Appl. No.: 11/893,207

(22) Filed: Aug. 15, 2007

(65) Prior Publication Data

US 2008/0069911 A1 Mar. 20, 2008

(30) Foreign Application Priority Data

Sep. 15, 2006 (TW) .............................. 95134243 A

(51) Int. Cl.
*A01N 65/10* (2006.01)
(52) U.S. Cl. .................................................... 424/725
(58) Field of Classification Search ....................... None
See application file for complete search history.

(56) References Cited

U.S. PATENT DOCUMENTS 6,096,334 A 8/2000 Rolf et al.

2006/0099283 A1 * 5/2006 Wei et al. ..................... 424/774

OTHER PUBLICATIONS

Oh, H. M., et al. "*Agastache rugosa* Leaf Extract Inhibits the iNOS Expression in ROS 17/2.8 Cells Activated with TNF-α and IL-1β" *Arch. Pharm. Res.* 28, (2005), pp. 305-310.
Lukhoba CW, et al. "Plectranthus: A Review of Ethnobotanical Uses" J Ethnopharmacol 2006; 103: 1-24.
Chang, Ja-Ming, et al. "Potential Use of *Plectranthus amboinicus* in the Treatment of Rheumatoid Arthritis" Original Article 6 pgs. Published Nov. 23, 2007.
Vera R, Mondon JM, Pieribattesti JC, Chemical Composition of the Essential Oil and Aqueous Extract of *Plectranthus amboinicus* Plant Med. 1993;59:182-3.
Wikipedia Article "Plectranthus Amboinicus".
Wikipedia Article "Agastache Rugosa".

* cited by examiner

*Primary Examiner*—Michael V Meller
*Assistant Examiner*—Qiuwen Mi
(74) *Attorney, Agent, or Firm*—Ladas and Parry LLP

(57) ABSTRACT

A pharmaceutical composition comprising a crude extract or extract of *Plectranthus Amboinicus* (Lour.) Spreng (PA) for the treatment of rheumatoid arthritis is described. The use of the crude extract or extract of *Plectranthus Amboinicus* (Lour.) Spreng for the manufacture of medicaments for treating rheumatoid arthritis is also described.

3 Claims, 17 Drawing Sheets

PLANT EXTRACTS FOR THE TREATMENT OF RHEUMATOID ARTHRITIS

BACKGROUND OF THE INVENTION

1. Field of the Invention

The present invention relates to Chinese herbal medicine extracts. In particular, the present invention relates to a use of the crude extracts or extracts of *Plectranthus Amboinicus* (Lour.) Spreng (PA) for treating rheumatoid arthritis (RA).

2. Description of the Prior Art

As a result of the use of various palliative medicaments and immunosuppressive agents, the treatment of rheumatoid arthritis has made great progress. Most studies reveal that when palliative medicaments or immunosuppressive agents are used as soon as the early outbreak, the destruction rate of bones can be effectively reduced. At present, the medicaments for treating rheumatoid arthritis are classified into the following three groups:

1. Non-steroidal anti-inflammatory drugs (NSAIDs), for example, aspirin, indomethacin, or naproxen, which can effectively inhibit inflammation and alleviate pain effect.

2. Anti-rheumatic drugs (ARDs), referred to as disease modifying anti-rheumatic drugs (DMARDs), for example, gold preparation, hydroxychloroquine, methotrexate (MTX) or penicillamine, which can inhibit conditions and improve immune abnormalities.

3. Steroids, referred to as corticosteroids, which are anti-inflammatory, and can be used as immunosuppressive agents.

Additionally, clinically common palliative drugs include sulfasalazine, and immunosuppressive agents include cyclosporine, azathioprine, or cyclophosphamide. Furthermore, since some antibiotics, such as minocycline, can inhibit enzymes, inhibit bone absorption, and inhibit production of inflammatory substances, they can be used for treating rheumatoid arthritis as well. Many treatment models have been proposed for the use of medicaments and treatment timing, such as Sawtooth therapy, Step-down bridge therapy, staging therapy, and target therapy. The spirit of these treatment models undoubtedly is to use various palliative medicaments or immunosuppressive agents alone or in combination in the early stages.

However, the shortcoming of these medicaments is that side effects will be caused as they work, especially steroids. Frequently, anti-inflammatory medicaments cause abnormalities in the bowel tract, e.g., bleeding, and the like.

A protein antagonist, such as TNF-α, could be also used clinically to palliate conditions rapidly, but it needs to be used in an invasive mode, which is inconvenient. Additionally, as the herb Radix Tripterygii Wilfordii has anti-inflammatory, bactericidal, and fever and pain relief effects, it is currently used for treating rheumatoid arthritis; however, security considerations may be taken due to its toxic side effect.

According to statistics, 1% of the population suffers from rheumatoid arthritis across the world. Accordingly, it is of great importance to develop convenient, safe, and efficient medicaments for treating rheumatoid arthritis.

*Plectranthus Amboinicus* (Lour.) Spreng (PA) originates in Malaysia and India, and is frequently planted by average families as an ornamental herb. The common herb PA is the epigeal portion of the *Plectranthus Amboinicus* (Lour.) Spreng plant, the aliases of which are Lysimachia capillipes Hemsl, Spearmint, Patchouly, Indian peppermint, or pogostemon cablin. East Indians use this as a cloth-perfuming agent, and the English found PA's charming scent after they introduced shawl cloth from India in 1820. If the leaves of PA were placed into the clothes directly, not only did the clothes acquire a scent, but also, the clothes were prevented from being moth-eaten. The PA is considered as having bactericidal, exciting, or insect repelling functions in Southeast Asia. Also, PA can cure bites from vipers or mosquitoes and insects, and also can relieve headaches, flatulence, vomiting, diarrhea, and fever, and the like. *Plectranthus Amboinicus* (Lour.) Spreng essential oil is the most popular flavor in Asia. In aromatherapy, PA is used to facilitate epithelial cell regeneration, and the treatments of acne, eczema, Hong Kong foot, and dry cracking of skin. Even more, PA is an excellent anti-depressant and aphrodisiac that functions to relieve anxiety and enhance libido.

In the present invention, it is unexpectedly found that crude extracts or extracts of PA have the efficacy of treating RA.

SUMMARY OF THE INVENTION

One object of the invention is to provide a pharmaceutical composition for treating rheumatoid arthritis, comprising a therapeutically effective amount of a crude extract or extract of *Plectranthus Amboinicus* (Lour.) Spreng (PA).

Another object of the invention is to provide a use of the crude extract or extract of PA for the manufacture of medicaments for treating rheumatoid arthritis.

Yet another object of the invention is to provide a method for manufacturing the crude extract or extract of PA.

The invention will be illustrated in detail below. Other features, objects, and advantages of the invention will be apparent from the specification and the claims.

DETAILED DESCRIPTION

Figure 1:
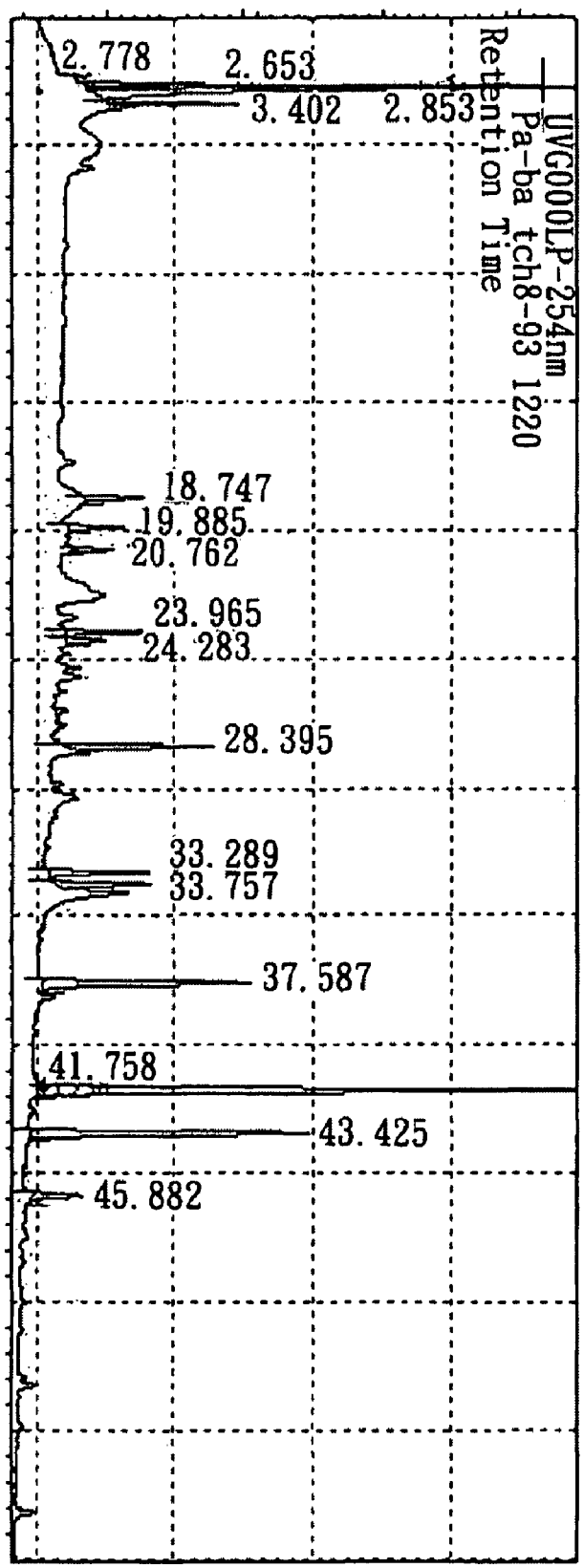
FIG. 1 is an HPLC pattern of the PA crude extract of Embodiment 1.

The term "treatment" or "treating," as used herein, refers to improving conditions.

The term "patient," as used herein, refers to animals, especially mammals. In a preferred embodiment, the patient is human.

The term "therapeutically effective amount," as used herein, refers to the amount of components of the pharmaceutical composition of the invention alone or in combination with other medicaments that could provide therapeutical benefits in treatment.

The term "carrier" or "pharmaceutically acceptable carrier," as used herein, refers to diluents, excipients, acceptable agents or the like that are wellknown by those of ordinary skill in the art and can be used in the preparation of pharmaceutical composition.

The term "PA crude extracts" or "PA extracts," as used herein, refers to those obtained by direct juice pressing or an extracting process used on the epigeal portion of the PA plant.

The term "high-polarity solvent," as used herein, refers to a solvent that has the highest polarity in the solvents used in the preparation process. The high-polarity solvent includes, but are not limited to water, methanol, ethanol, or a mixture of two or more of the preceding solvents.

The term "low-polarity solvent," as used herein, refers to a solvent that has the lowest polarity in the solvents used in the preparation process. The low-polarity solvent includes, but are not limited to chloroform, isopropanol, acetone, ethyl acetate, a mixture of two or more of the preceding solvents, or a mixture of one or more of the preceding solvents with one or more solvent that have higher polarity in a ratio (v:v) from about 70:30 to about 50:50.

The term "sub-high-polarity solvent," as used herein, refers to a solvent that has a polarity lower than that of the high-polarity solvent used in the preparation process but higher than that of the medium-polarity solvent used in the preparation process. The sub-high-polarity solvent can be obtained by mixing a high-polarity solvent with a solvent having lower polarity in a ratio (v:v) from about 70:30 to about 30:70, preferably from about 60:40 to about 40:60.

The term "medium-polarity solvent," as used herein, refers to a solvent that has a polarity lower than that of the sub-high-polarity solvent used in the preparation process but higher than that of the low-polarity solvent used in the preparation process. The medium-polarity solvent can be obtained by mixing a high-polarity solvent with a solvent having lower polarity in a ratio (v:v) from about 30:70 to about 5:95, preferably from about 15:85 to about 5:95.

The invention is characterized by the use of PA crude extracts or PA extracts for treating RA. Thus, the invention provides a pharmaceutical composition for treating RA, comprising a therapeutically effective amount of a PA crude extract or PA extract.

The most suitable route and dosage for treatment will be easily determined by those skilled in the art. According to the invention, the preferred route is oral administration, for example, but not limited to, capsule, tablet, powder, ointment, liquor, or spray, etc. Dosage will depend on the nature and states of the symptoms being treated, ages and general physical conditions of the patient being treated, administration route and any therapies practiced previously. It should be understood by those skilled in the art that the dosage will vary with patients, depending on age, size, health condition, and related factors. Furthermore, if desired, the composition could be sterilized, or mixed with any pharmaceutically acceptable carrier or excipient. The preparation of the pharmaceutical composition of the invention can be performed by those skilled in the art according to conventional methods.

In preferred embodiments of the invention, the preparation of PA crude extracts and PA extracts is shown as follows.

Preparation of PA Crude Extract

A fresh PA plant was taken, washed with clean water, and then pressed by a juice extractor to obtain juice. The PA juice then was freeze-dried, to provide a dry powder, which was taken up in an appropriate solvent, such as chloroform or methanol, to give the PA crude extract.

Preparation of PA Extract

A certain amount of dry PA was soaked in a suitable amount of a high-polarity solvent, filtrated, and then soaked again in a suitable amount of a high-polarity solvent. After this, the PA extract liquor was condensed to 2-3% of its original volume under reduced pressure by a rotary concentrator, diluted in a solvent, and then separated in a column. Optionally, four segments of different solvents from high polarity to low polarity (referred to as high-polarity solvent, sub-high-polarity solvent, medium-polarity solvent, and low-polarity solvent) could be used for elution continuously. The high-polarity solvent, sub-high-polarity solvent, medium-polarity solvent, and low-polarity solvent are as defined above. Preferably, the column separation method uses a DIAION column that has already been treated by methanol. For example, the same amount of DIAION as dry PA was weighed out, soaked in methanol, and then filled into a column. After the filling, the DIAION was washed with 1-2 times volume of methanol, followed by 5-6 times volume of deionized and distilled water. Once the washing was finished, the filling was complete.

Ingredient Analysis of the Extracts of PA Medicinal Material

Instrument and Apparatus

High performance liquid chromatograph

Pump: Spectra-Physics P4000

Detector: UV/VIS Spectra-Physics Spectra System UV600OLP

Automated sampler: Thermo Separation Pruducts AS3500

Software: Thermo Separation Pruducts Chrom Quest

System control: Thermo Separation Pruducts SN4000

Conditions of liquid chromatography

Chromatograph column: COSMOSIL, 4.6×250 mm, 5C18-MS

Flow rate: 1.0 ml/min Pressure Limite: 250 kgf/cm$^2$

Sample injection: 10 μl

PDA condition:

Sampling: 0.64 sec

Wavelength range: 190-370 nm uv wavelength: 254 nm

Elution Condition (1):

| | Time (min) | | | |
|---|---|---|---|---|
| Mobile phase | 0 | 15 | 55 | 60 |
| Water | 90% | 90% | 20% | 80% |
| Acetonitrile | 10% | 10% | 80% | 20% |

Elution Conditions (2):

|  | Time (min) | | | |
| --- | --- | --- | --- | --- |
| Mobile phase | 0 | 11 | 20 | 30 |
| Water | 95% | 67% | 67% | 60% |
| Acetonitrile | 5% | 33% | 33% | 40% |

The invention is described in detail with reference to the following non-limiting examples. The following procedures could be carried out to verify the effect of PA crude extracts or extracts on treating RA. Any modifications and changes that can be easily achieved by those skilled in the art are included in the scope of the disclosure of the specification and appended claims.

EMBODIMENT

Embodiment 1

PA Crude Extracts Obtained by Using Direct Juice Pressing 1.25 kg fresh PA was weighed, washed with clean water, and then pressed by a juice extractor to obtain juice. A volumetric cylinder was used to measure the volume of the juice, from which 1050 ml was taken out, and was freeze-dried, to obtain 19 g dry powder (yield of 1.5%). The HPLC pattern is shown in FIG. 1.

Embodiment 2

Animal Test on Treating RA in Animals by PA Crude Extracts

[Test Animal]
The test animals, Lewis rats, 8 weeks old and about 155-165 g in weight, were all purchased from National Laboratory Animal Center. They were raised in an animal house with a 12-hour light/12-hour dark cycle, a room temperature of 23±1° C., moderate moisture, and good air conditioning, wherein water and feed were provided ad libitum. In addition, during the operation, all the test animals conformed to the criteria of the International Committee on Laboratory Animals' standard regulation.

[Medicaments]
1. Collagen Type II (Sigma C-1188), obtained from bovine tracheal cartilage
2. Complete Freund's adjuvant, CFA (BD BBL™ 231131)
3. Incomplete Freund's adjuvant, IFA (BD BBL™ 263910)
4. ELISA kit of tumor necrosis factor (TNF-α), interleukin-6 (IL-6), and interleukin-1β(IL-1β) of rat (R&D, Duoset)
5. C-reactive protein (CRP) of rat, ELISA kit (BD™ Pharmingen 557825)
6. Indomethacin (commercially available from Johnson Chemical Pharmacy Corporation, Sanchung City, Taipei County)
7. Fresh Chinese herb PA was pressed directly to obtain juice, concentrated under reduced pressure to form a PA concentrated solution, and then diluted into a high concentration of 22.5 g crude medicine/kg (PA-H) and a low concentration of 4.5 g crude medicine/kg (PA-L), respectively. Finally, the solutions were directly administered orally to the rats based on respective actual body weights.

[Apparatus]
1. Syringe: 1 ml, 3 ml, and 5 ml (Terumo)
2. Balance
3. Vernier Caliper (Mitutoyo Corporation)
4. Three-way piston tube
5. Oscillator (Vortex)
6. ELISA reader (Dynex, Thermo Labsystems)

[Protocol]
1. Antigen Formulation and Immune Injection

Figure 2:
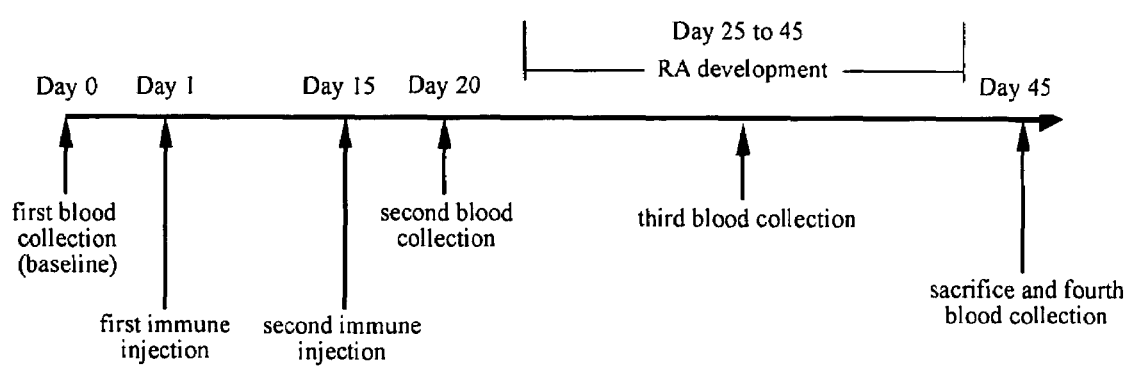
FIG. 2 illustrates a scheme of the animal test of Embodiment 2.

The animal test scheme is shown as FIG. 2. Bovine collagen Type II (Bovine C II) was dissolved in 0.1 M acetic acid solution, stirred to dissolve thoroughly, and formulated into solutions with concentrations of 1.5 and 3 mg/ml, which were stored in 4° C. for later use. For the first immune injection, 100 µl of C II solution was emulsified with an equal amount of CFA, and injected subcutaneously (200 µl/rat) in the root portions of tails of the rats after the emulsification was complete. After the first immunization, the body weights of the rats were recorded every three days, and they were observed in order to discover whether or not swelling occurred in limbs. After about 15 days, the second immunization was done. 100 µl of C II solution was emulsified with an equal amount of IFA, and injected subcutaneously (200 µl/rat) in the root portions of tails of the rats after the emulsification was complete. Approximately from Day 20, the symptoms of arthritis were observed (CIA rats), and PA and indomethacin were fed until Day 45.

2. Grouping and Treating of Animals

| Group | Treatment | Gavage |
| --- | --- | --- |
| A | Normal rats (blank) | Normal gavage |
| B | CIA rats + vehicle (control group of disease generating) | distilled water |
| C | CIA rats + indomethacin (control group of commercial medicine) | indomethacin, 2.5 mg/kg/day |
| D | CIA rats + PA-L | PA, 75 mg/kg/day |
| E | CIA rats + PA-H | PA, 375 mg/kg/day |

N = 3 rats/group

[Test Items and Indices]
1. Body weight observation: shown by weighing every 3 days
2. Evaluation of RA examination: evaluated in maximum arthritic index (MAI)
3. Joint swelling rate: measured by Vernier Caliper (Day 15-28 arthritis development)
4. Rheumatoid factor (RF)
5. Acute inflammatory C-reactive protein (CRP)
6. Cytokine: TNF-α, IL-1β, and IL-6 (inflammatory cytokine)

Evaluation of RA Examination

After immunization, the rats were observed three times a week. The changes of redness and swelling or the like in limbs were recorded, and photographs were taken and filed for comparison. The scoring of the examinations was based on 5 grades as follows:

0: No symptom of arthritis occurs.
1: Sole and tarsus show red and swell slightly.
2: Tarsus and ankle are red and swell moderately.
3: Tarsus and ankle are red and swell severely.
4: Joints are stiff, and bones deform.

Maximum arthritic index, average MAI for each group was calculated as follows:

Average MAI=Total of MAI recorded in limbs of each rat (0: no CIA occurs, 16: highest score)/4/total rat number of each group Measurement of Arthritic Swelling Degree The thickness changes of soles of rats were measured by a Vernier Caliper (twice per week), and there were eight measurement sites in total in each rat, including one site at the center of each sole of the two front feet respectively, and three sites in each of the two back feet (ankle joint, sole, and root portion of toe) respectively.

Serum RF Analysis

1. Collagen was formulated in a coating buffer to a concentration of 40 μg/ml, 0.1 ml of which was added into a 96-well micro plate respectively, and was kept in 4° C. overnight.

2. After washing with Tris buffer three times, 0.2 ml of blocking buffer containing 1% BSA was added into each well. The reaction lasted for 2 hours at room temperature, and then was washed by Tris buffer three times again.

3. After the serum sample was diluted appropriately with Tris buffer containing 0.05% Tween 20 (1/20 or 1/40), 0.1 ml serum sample was added into each well of the 96-well micro plate. The reaction lasted for 2 hours at room temperature, and then was washed by Tris buffer three times again.

4. Coated anti-rat immunoglobulin M (IgM) was combined with horseradish peroxide (HRP), appropriately diluted (1/12000), and then added into the 96-well micro plate. The reaction lasted 2 hours at room temperature, and then was washed by Tris buffer three times again.

5. 0.1 ml of tetramethyl benzidine (TMB) was directly added into each well for color reaction, and then a stopping solution was added to stop the reaction. Finally, absorption (O.D) value was read out at the wavelength of 450 nm.

Serum C-Reactive Protein (CRP) Analysis

1. CRP ELISA kit was a pre-coated microplate, into which 0.1 ml of appropriately diluted serum sample could be added directly. After being reacted for 1 hour at room temperature, it was washed by the washing buffer four times.

2. Rabbit anti-rat C-reactive protein (CRP) was combined with HRP Ab, diluted with the washing buffer 100 times, and then 0.1 ml was added into each well. After being reacted for 1 hour at room temperature, it was washed by the washing buffer four times.

3. 0.1 ml of TMB was added into each well for color reaction, and after about 5 to 10 minutes, a stopping solution was added to stop the reaction. Finally, O.D value was read out at the wavelength of 450 nm.

(The above analyzing methods were all carried out according to the examination regulations appended to the kit)

Abdominal Cavity Cell Culture and Cytokine Analysis

1. After carbon dioxide euthanasia, the outer furs of the rat abdominal cavity were cut out by scissors, to expose the whole abdominal cavity.

2. HBSS buffer was injected into the abdominal cavity batch-wise by a 10 ml syringe to make a total volume of about 20 ml/rat.

3. The abdominal cavity of the rat was opened after the abdomen was gently kneaded. An incision of about 2 cm was made in the abdominal cavity by using scissors. Peritoneal exudation cell (PEC) liquid (about 10 to 15 ml of cellular fluid could be collected) was drawn with a syringe, and placed into a 50 ml centrifuge tube.

4. The supernatant was removed after the liquid was centrifuged at 1500 rpm for 5 minutes. 10 ml of HBSS buffer was added to wash, and then centrifuged, after which the supernatant was removed.

5. The cell concentration was adjusted to $2 \times 10^6$ cells/ml with a fresh culture medium (containing antibiotics).

6. The cell suspension was divided into a 48-well plate at 0.5 ml/well.

7. An additional. 0.5 ml of lipopolysaccharides (LPS) (20 μg/ml) was added separately, making a final concentration of 10 μg/ml.

8. Finally, it was placed into a 37° C. incubator for 24 hours. The supernatant was collected, and stored in −20° C. The concentrations of cytokine TNF-α, IL-6, and IL-1β were analyzed by using ELISA kit.

[Results and Discussion]

I. Changes in the Body Weight of Rats

Figure 3:
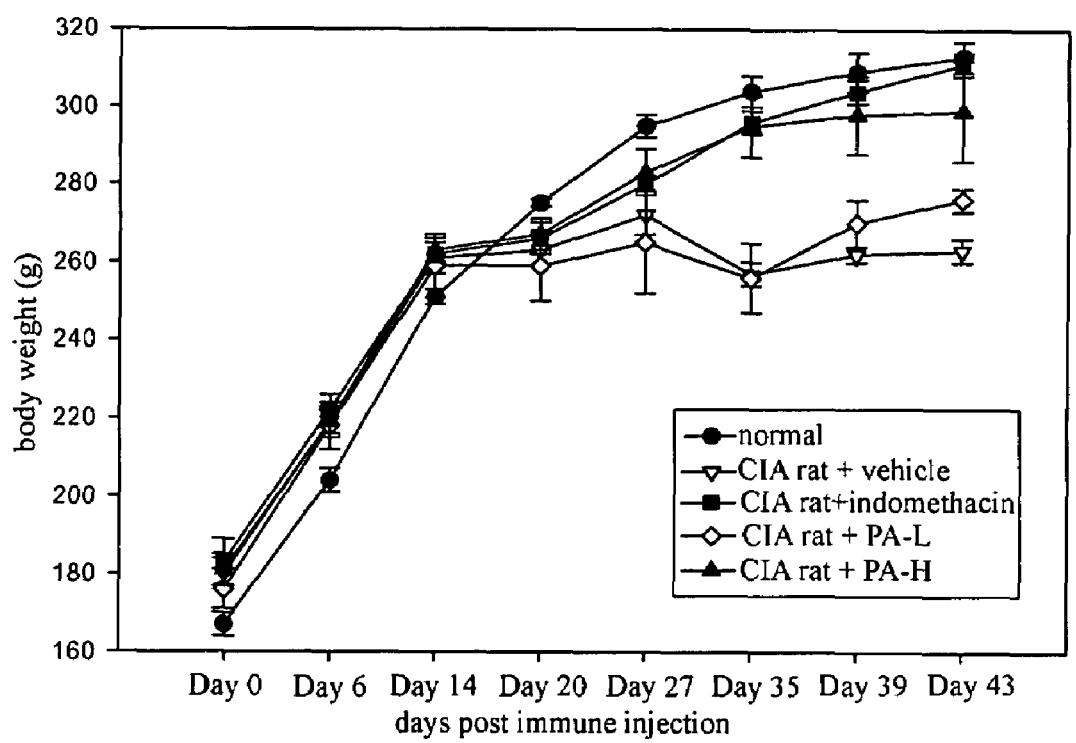
FIG. 3 illustrates the effect of feeding on PA crude extracts on the body weight of CIA rats.

In the animal test, both applying drugs and applying other outer forces affect the changes of body weight directly or indirectly. Therefore, the observation of body weight directly is the most important index in appearance. The results of measurement of body weight show that the arthritis symptoms induced by collagen occur after about Day 20, and compared to normal rats, their body weights are reduced significantly, as shown in FIG. 3; however, weight reduction is efficiently avoided in the groups of rats fed with PA-H and indomethacin, with the same growth curve as the normal group. In addition, the weight reduction phenomenon could not be efficiently inhibited in the group fed with PA-L.

II. Maximum Arthritic Index

Figure 4:
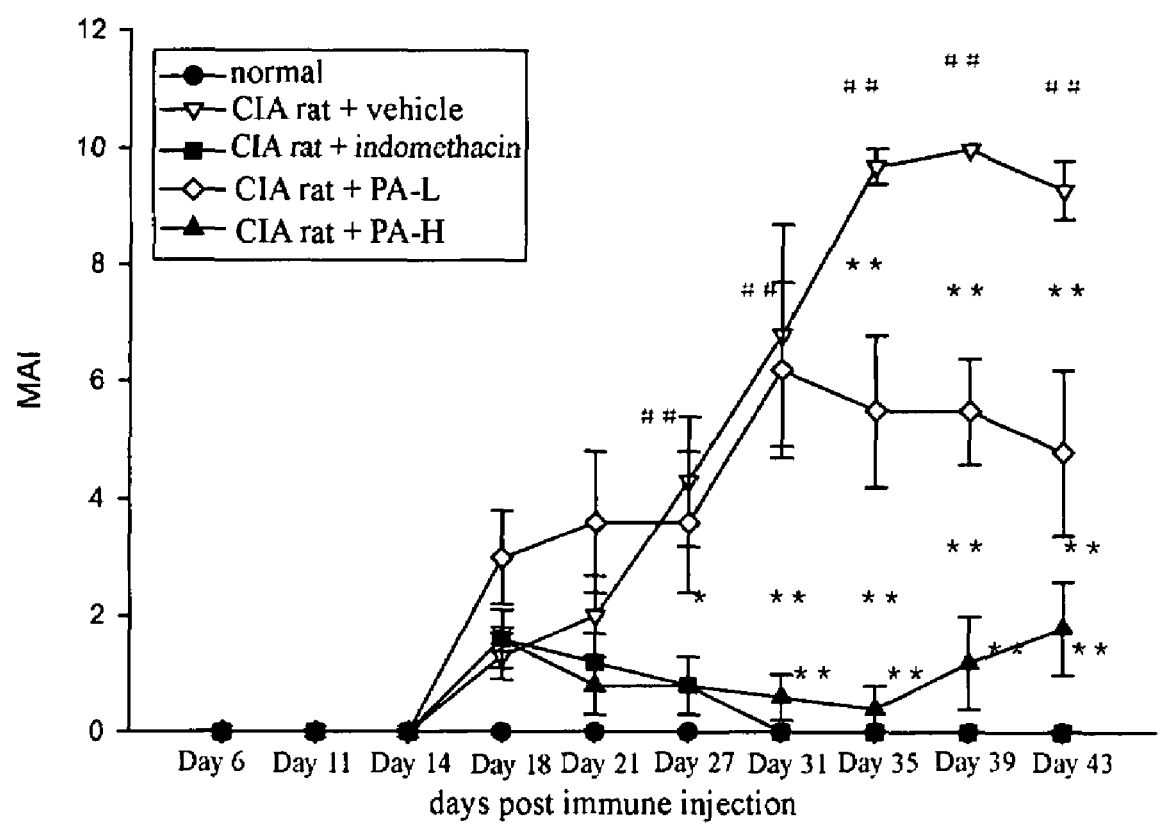
FIG. 4 illustrates the effect of feeding on PA crude extracts on the arthritic indices of CIA rats.

As described in the section of Material and Method, maximum arthritic index (MAI), with a 5-stage difference as the criterion for examination scoring, is one of the appearance indices. As shown in FIG. 4, the arthritis of rats induced by collagen reaches a peak at about Day 35, while the arthritic indices could be efficiently reduced in the groups of rats fed with PA and indomethacin, wherein the results of PA-H and indomethacin are most preferred.

III. Joint Swelling Degree

Figure 5:
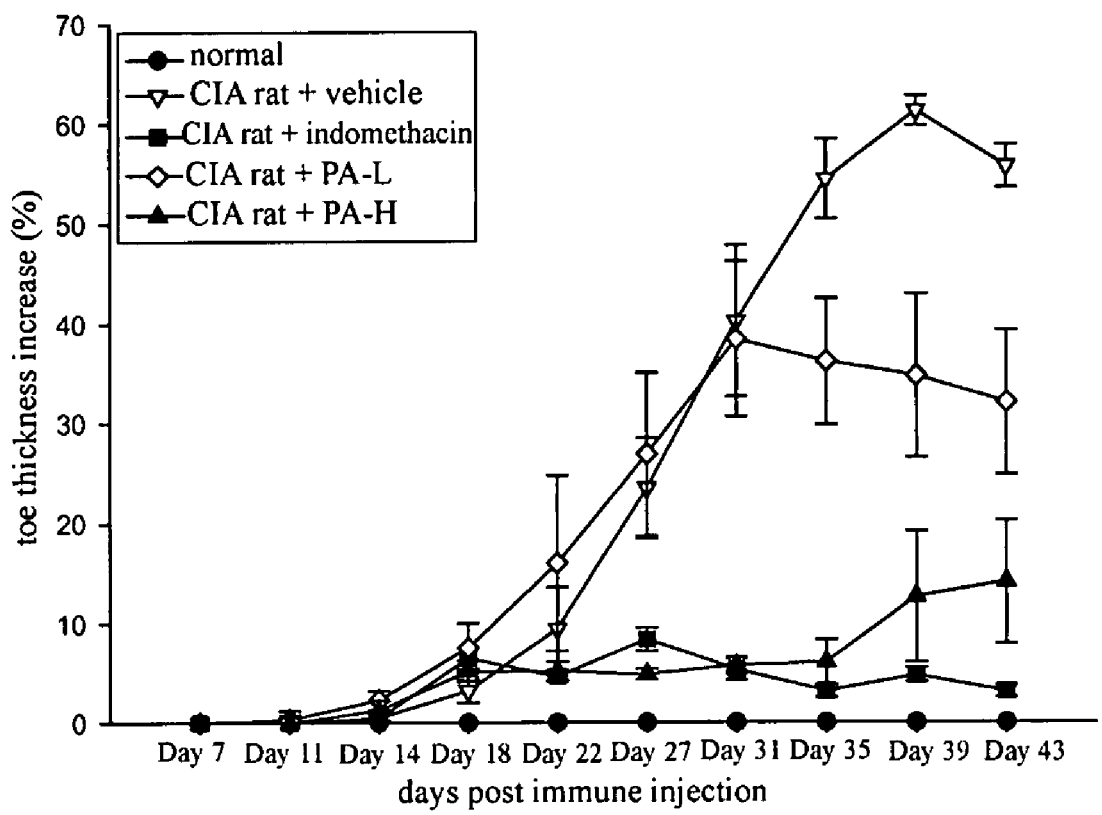
FIG. 5 illustrates the effect of feeding on PA crude extracts on the arthritic swelling degree of CIA rats.

Arthritis symptoms occurred successively at about Day 20 after the second antigen injection of rats, and the joint sites of limbs were actually measured with a Vernier Caliper. Joint swelling rate (the average obtained from 8 measurement sites) increased from 20% to the highest, 61%, in Day 39, and as shown in FIG. 5, it has a significant difference compared to the normal group (P<0.01). From the view of feeding on PA and indomethacin, both PA-H and PA-L can efficiently inhibit the joint swelling, wherein the effects of PA-H and indomethacin are still most preferred, suggesting that PA-H may have a similar anti-inflammatory effect to indomethacin.

IV. Effect of Feeding on PA on Serum RF

Figure 6:
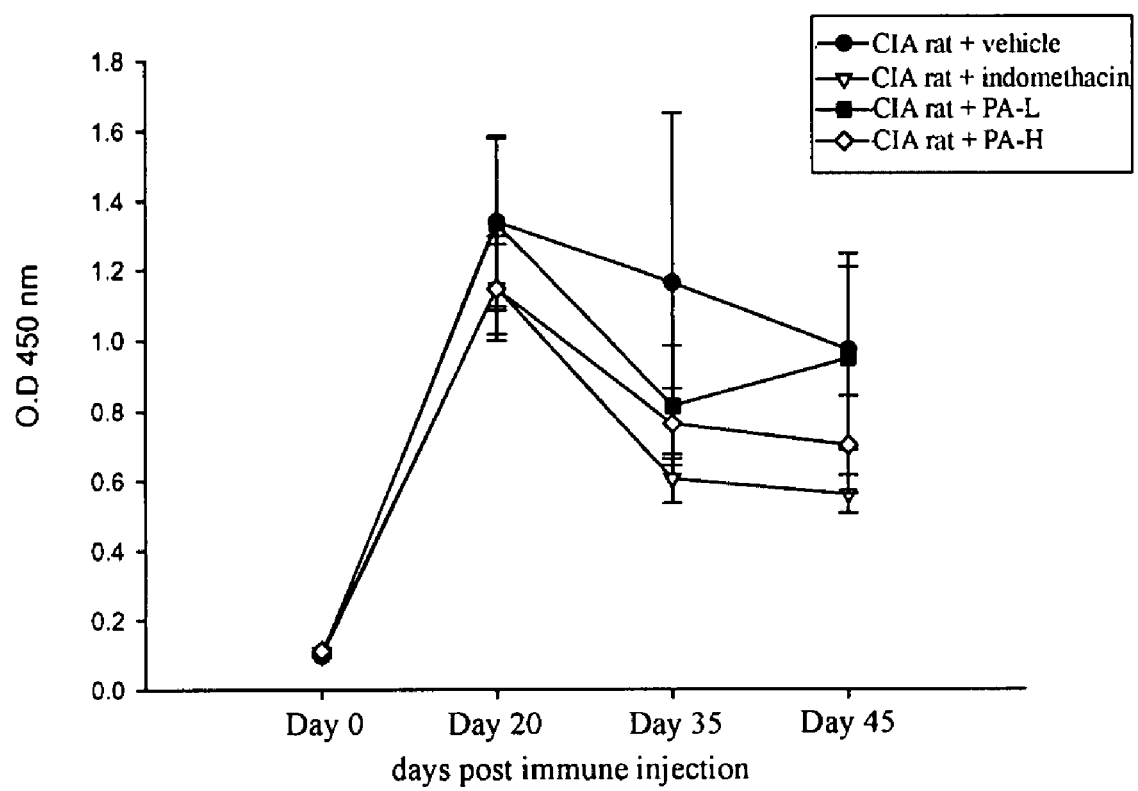
FIG. 6 illustrates the effect of feeding on PA crude extracts on the serum RF of CIA rats.

During RA development, there are several autoantibodies that occur. However, in clinical diagnosis, the presence or absence of an autoantibody in patient serum is a major criterion in determining whether it is RA or not, wherein the autoantibody of RF is most important. Therefore, the animal model of CIA in the present test also takes RF as an important biochemistry index. It has been pointed out in past studies that the RF in human or rat serum could be analyzed using ELISA method (Vittecoq et al., 2001; Jonsson et al., 1986). In the present study, we made some improvements on the basis of past analysis methods, and rebuilt a technological platform for rat serum RF analysis. The analysis results show that at Day 20 after two antigen injections, the serum RF titers of rats all reach a peak, as shown in FIG. 6; however, compared with Day 20, at Day 35, the serum RF values of the groups fed with PA and indomethacin reduced by 33% and 47% respectively, and at Day 45, further reduced by 39% and 51% respectively. In addition, the present study found that the serum RF value of the negative control group has the tendency of gradual reduction from Day 20, suggesting that after arthritis symptoms are induced by collagen in rats, the symptoms tend to be relieved and even recover over time; as a result, it is assumed that the "golden time" for disease development is Day 20 to Day 45.

V. Effect of Feeding on PA on Serum CRP

Figure 7:
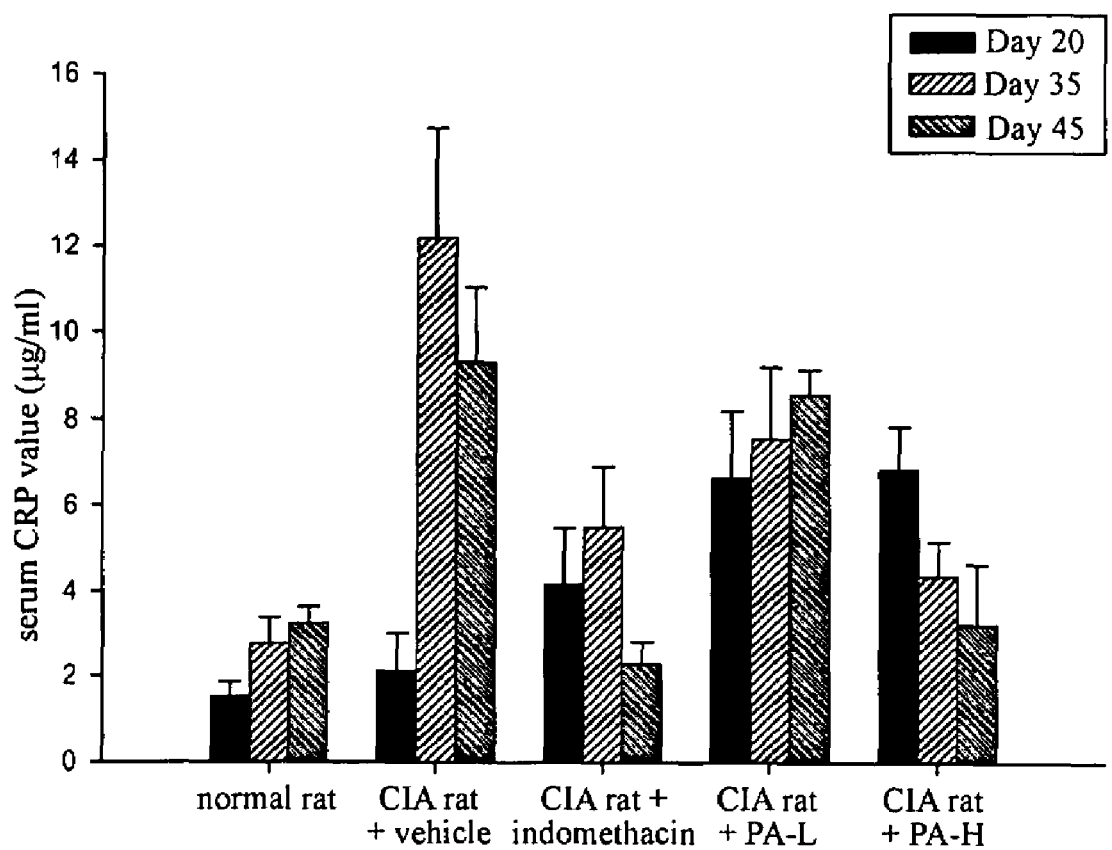
FIG. 7 illustrates the effect of feeding on PA crude extracts on the serum CRP of CIA rats.

Serum CRP is mainly produced by the liver, and is an index of causing systemic inflammatory response; if is the most important reactant presented in serum during acute inflammation. It is noted in some references that the CRP level in the serum of RA patients, and the production of IL-1 and TNF-α are closely related to arthritis disorder development (Nakamu, rheumatoid arthritis, 2000). The study results show that after two antigen immune injections, CRP concentration in rat serum is significantly increased, and reaches a peak at Day 35, as shown in FIG. 7, and it has a significant difference compared with the normal group (P<0.01). Also we found that at Day 35, after feeding on PA-H and indomethacin, the serum CRP concentration could be efficiently inhibited in CIA rats, and the same effects still exist at Day 45, suggesting that feeding on PA-H has the same treatment effect of clinical anti-inflammatory administration as indomethacin. Feeding on PA-L has no significant inflammatory inhibiting effect.

VI. Change of PEC Cytokine

Figure 8:
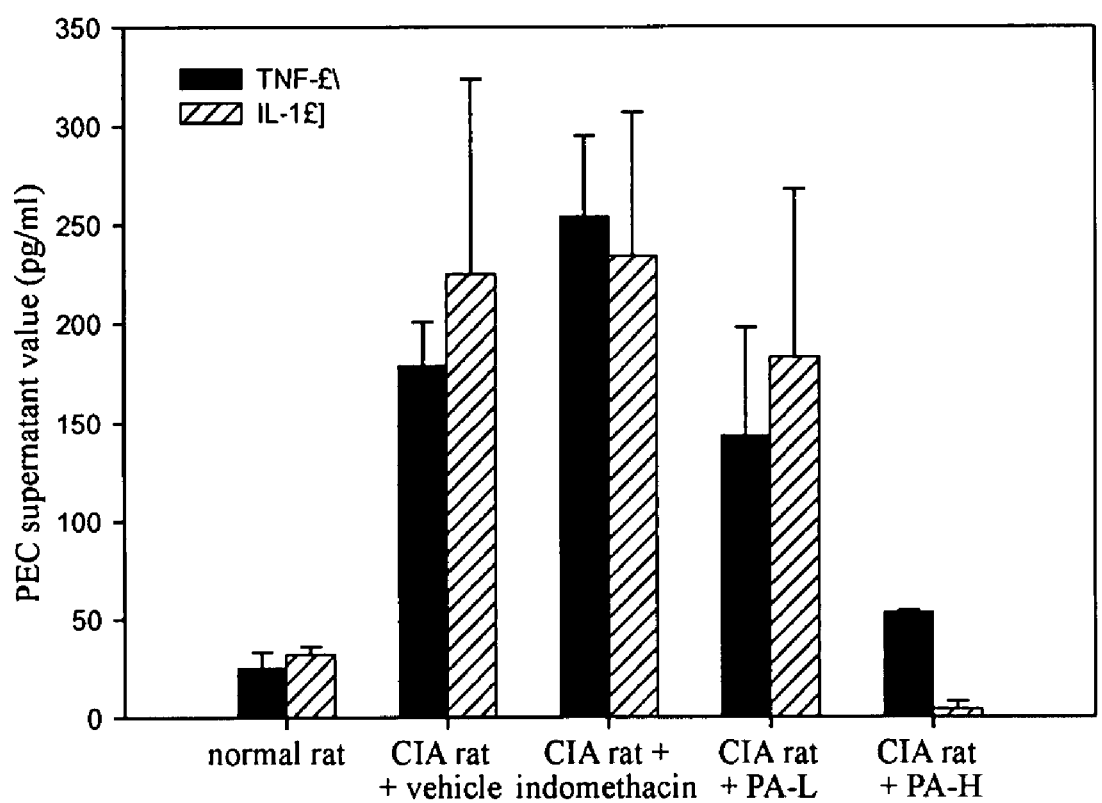
FIG. 8 illustrates the effect of feeding on PA crude extracts on cytokine TNF-α and IL-1β in the abdominal cavity of CIA rats.
Figure 9:
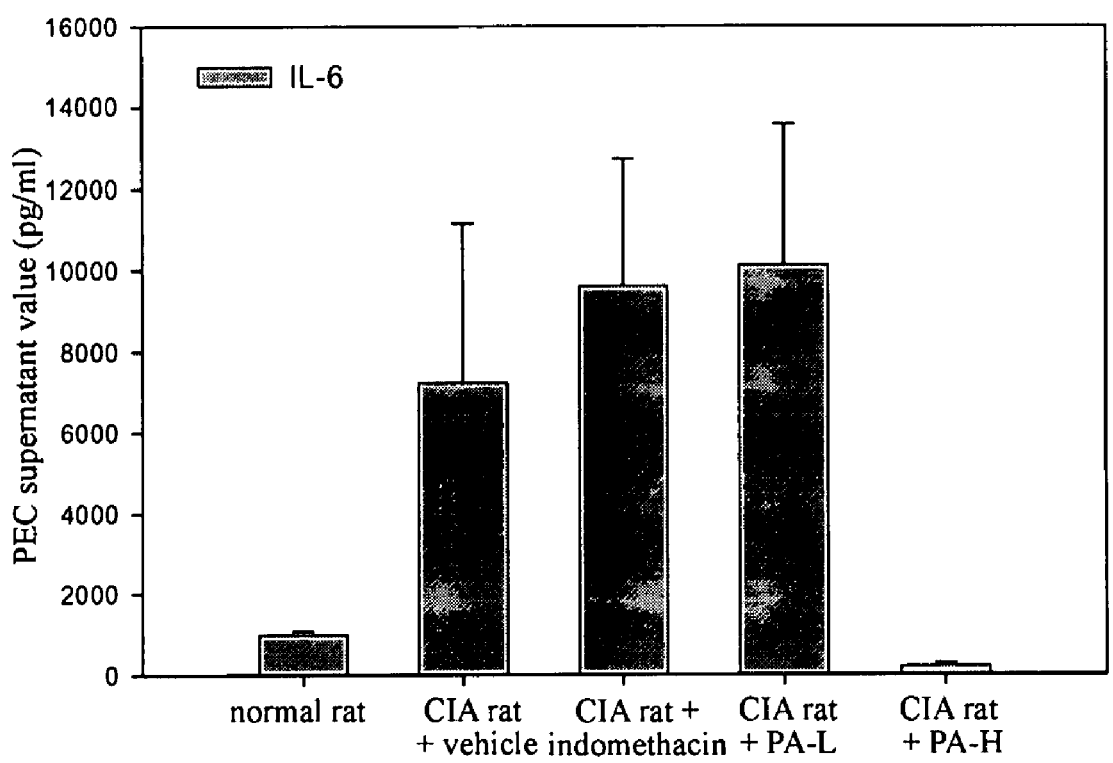
FIG. 9 illustrates the effect of feeding on PA crude extracts on cytokine IL-6 in the abdominal cavity of CIA rats.

Besides the several important biochemistry indices above evaluating whether PA has an anti-swelling or anti-inflammatory effect or not, the study also further explores the effect of the secretion of cytokine on inflammatory response, in order to more easily understand the change in states of rats before and after the occurrence of RA symptoms, wherein such inflammatory cytokines as TNF-α, IL-6, and IL-1β are the most important indices, i.e., the amount of these cytokines in the body is closely related to inflammatory response. The study results demonstrate that feeding PA-H to CIA rats can significantly inhibit PEC from secreting TNF-α and IL-1β (as shown in FIG. 8), as well as IL-6 (as shown in FIG. 9). Additionally, in the feeding with indomethacin, there was no effect of inhibiting PEC from secreting inflammatory cytokine, assuming that the effect mechanism of indomethacin was not directed to this; therefore, the application value of PA in anti-swelling or anti-inflammatory use is further emphasized.

It is known from the above that in the comparison of the drug of the present invention and indomethacin of the control group, the drug efficacy of highly concentrated PA crude extracts is equal to that of 2.5 mg/kg of indomethacin. In addition, indomethacin is an inhibitor of COX, and its pharmaceutical effect may be different from that of PA, based on the exhibited inhibiting phenomenon of cytokine.

Embodiment 3

PA Extracts (PA-EtOH, PA-F1, PA-F2, PA-F3, and PA-F4) Obtained by Using Column Separation Purification 2 kg of PA dry material was taken, soaked in 10 times highly concentrated ethanol for 24 hours, filtrated, and then soaked in 10 times highly concentrated ethanol for 24 hours again. After this, PA extract liquor is condensed to 2~3% of its origin volume under reduced pressure by a rotary concentrator, dried into a powder and named PA-EtOH, 30 g of weight, 1.5% of yield.

After being diluted with a solvent, it was filled into a DIAION column that was pretreated. It was washed with a high-polarity solvent with about 10 times volume of dry herb, and then the elution was collected, named PA-F1, 8.5 g of weight, 0.43% of yield.

Figure 10:
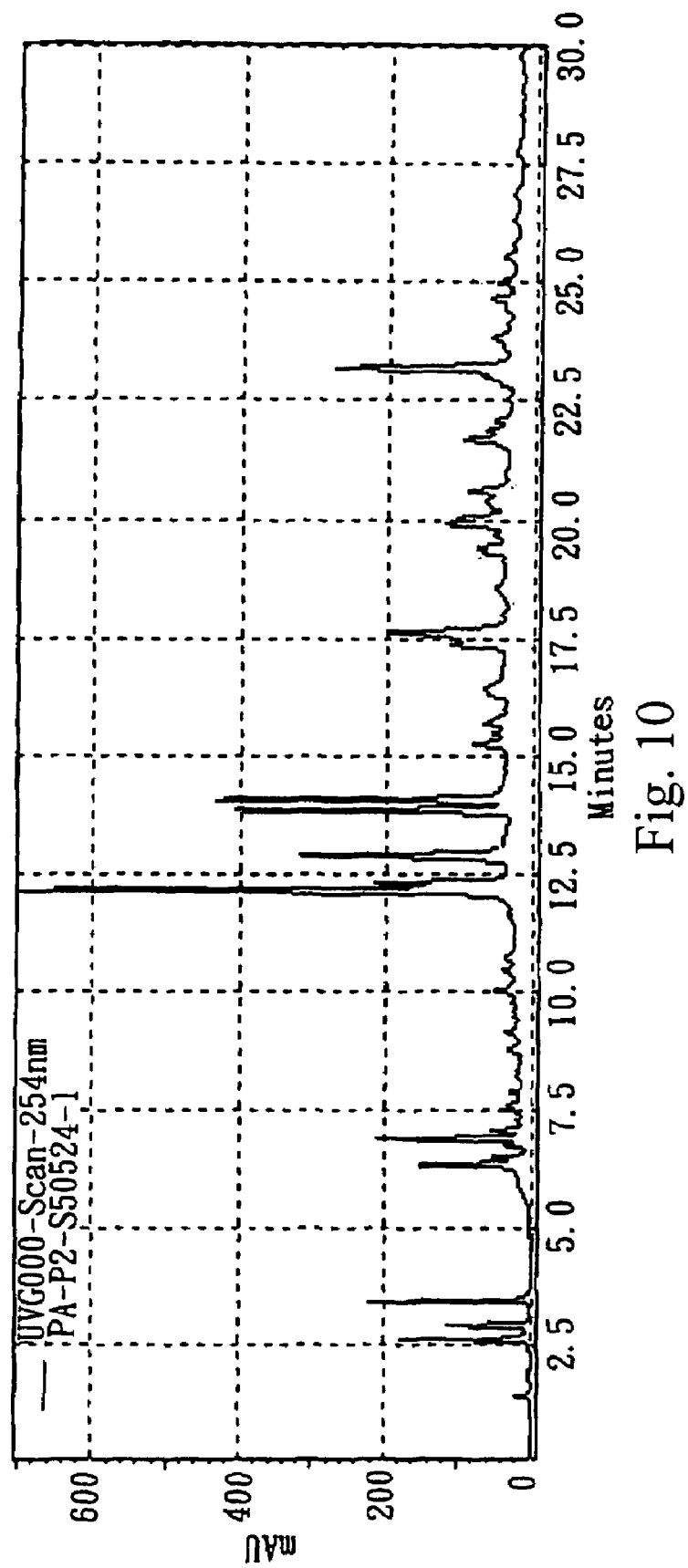
FIG. 10 is a HPLC pattern of the PA extract PA-F2 of Embodiment 3.

The column was washed with a sub-high-polarity solvent with about 5 to 10 times volume of dry herb, and the elution was collected, named PA-F2, 12 g of weight, 0.6% of yield. The HPLC pattern is shown in FIG. 10.

The column was washed again with a medium-polarity solvent with about 5 to 10 times volume of dry herb, and the elution was collected, named PA-F3, 15 g of weight, 0.75% of yield.

The column was washed again with a low-polarity solvent which is about 5 to 10 times volume of dry herb, and the elution was collected, named PA-F4, 12 g of weight, 0.6% of yield.

Embodiment 4

Animal Test of PA Extracts for Treating RA Animals

In the present animal test, the test animals and apparatus used are the same as those disclosed in embodiment 2.

[Medicaments]
1. Collagen Type II (Sigma C-1188), obtained from bovine tracheal cartilage
2. Complete Freund's adjuvant, CFA (BD BBL™ 231131)
3. Incomplete Freund's adjuvant, IFA (BD BBL™ 263910)
4. ELISA kit of interleukin-6 (IL-6) and interleukin-1β (IL-1β) (R&D, Duoset)
5. Ceelebrex (CBX)
6. PA extracts (PA-EtOH, PA-F1, PA-F, PA-F3, and PA-F4) in Embodiment 3, directly administered orally to the rats based on respective actual body weights.

[Protocol]
1. Antigen Formulation and Immune Injection

Figure 11:
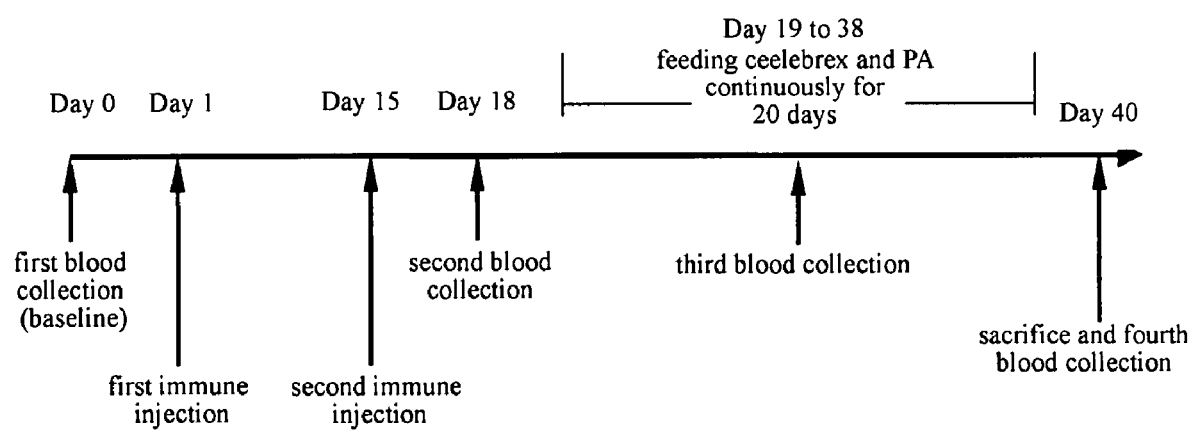
FIG. 11 illustrates a scheme of the animal test of Embodiment 4.

The animal test scheme is shown as FIG. 11. Bovine collagen type II was dissolved in 0.1 M acetic acid solution, stirred to dissolve thoroughly, and formulated into solutions of concentrations of 1.5 and 3 mg/ml, which were stored at 4° C. for later use. For the first immune injection, 100 μl of C II solution was emulsified with an equal amount of CFA, and injected subcutaneously (200 μl/rat) in the root portions of tails of the rats after the emulsification was complete. After the first immunization, the body weights of the rats were recorded every three days, and they were observed to discover whether or not swelling occurred in limbs. After about 15 days, the second immunization was done. 100 μl of C II solution was emulsified with an equal amount of IFA, and injected subcutaneously (200 μl/rat) in the root portions of tails of the rats after the emulsification was complete. Approximately from Day 18, the symptoms of arthritis were observed (CIA rats), and PA and CBX were fed from Day 19 until Day 38.

2. Grouping and Treating of Animals

| Group | Treatment | Gavage |
|---|---|---|
| A | CIA rats + PA-EtOH | PA, 40.5 mg/kg/day |
| B | CIA rats + PA-F1 | PA, 3.0 mg/kg/day |
| C | CIA rats + PA-F2 | PA, 1.13 mg/kg/day |
| D | CIA rats + PA-F3 | PA, 11.3 mg/kg/day |
| E | CIA rats + PA-F4 | PA, 11.3 mg/kg/day |
| F | CIA rats + H₂O | distilled water |
| G | CIA rats + CBX | CBX, 18 mg/kg/day |
| J | Normal rats (blank) | Normal gavage |

N = 3 rats/group

Figure 12:
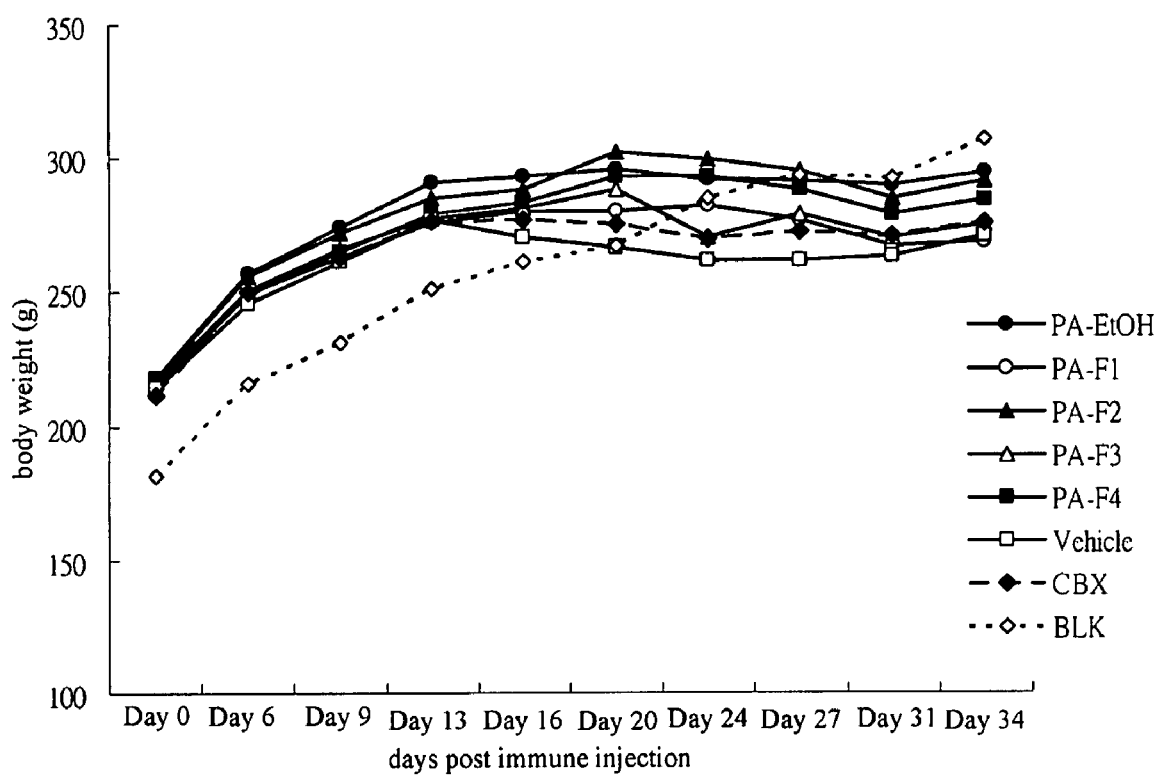
FIG. 12 illustrates the effect of feeding on PA extracts on the body weight of CIA rats.

[Results and Discussion]
I. Changes in the Body Weight of Rats
As shown in FIG. 12, there was no obvious difference between the body weights of normal rats and CIA rats in each group. In comparison with the control group that was fed distilled water, the rats fed with PA-EtOH, PA-F2, and PA-F4 have a heavier weight.

II. Maximum Arthritic Index

Figure 13:
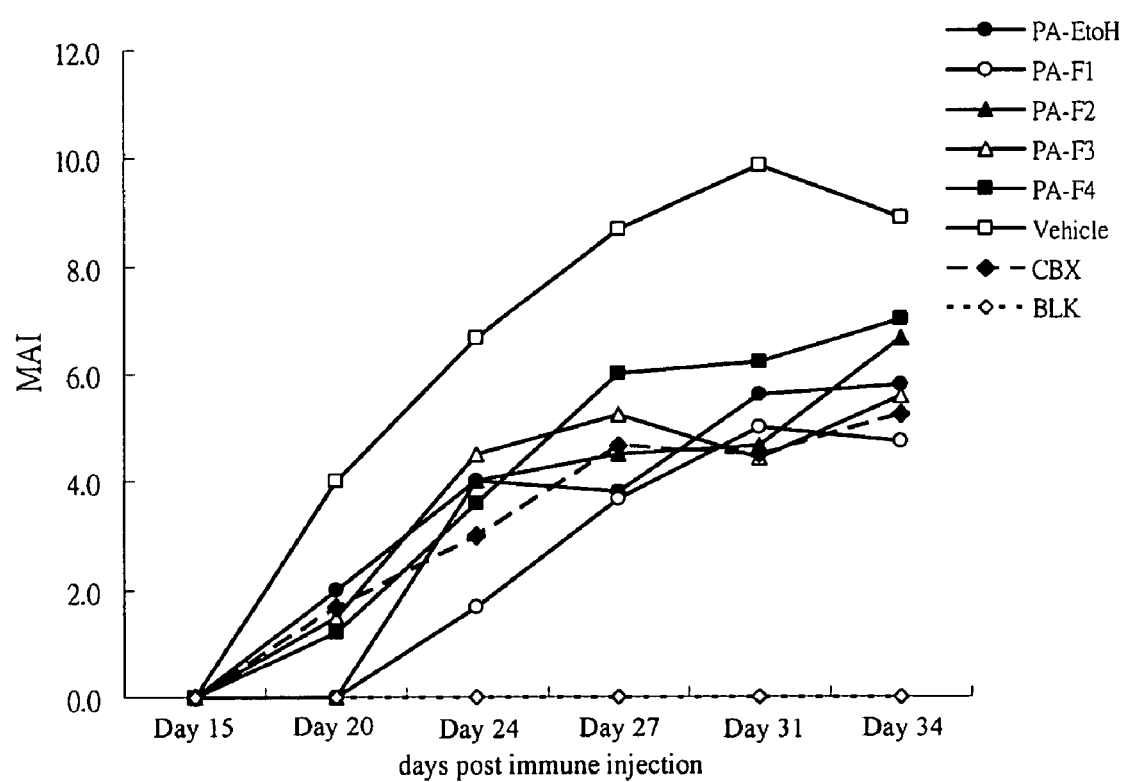
FIG. 13 illustrates the effect of feeding on PA extracts on the arthritic indices of CIA rats.

As shown in FIG. 13, the arthritis index of rats induced by collagen reaches a peak at about Day 31, while the arthritic indices could be efficiently reduced in the groups of rats fed with PA-EtOH, PA-F1, PA-F2, PA-F3, PA-F4, and CBX, wherein the results of PA-F1 and CBX are most preferred.

III. Joint Swelling Degree

Figure 14:
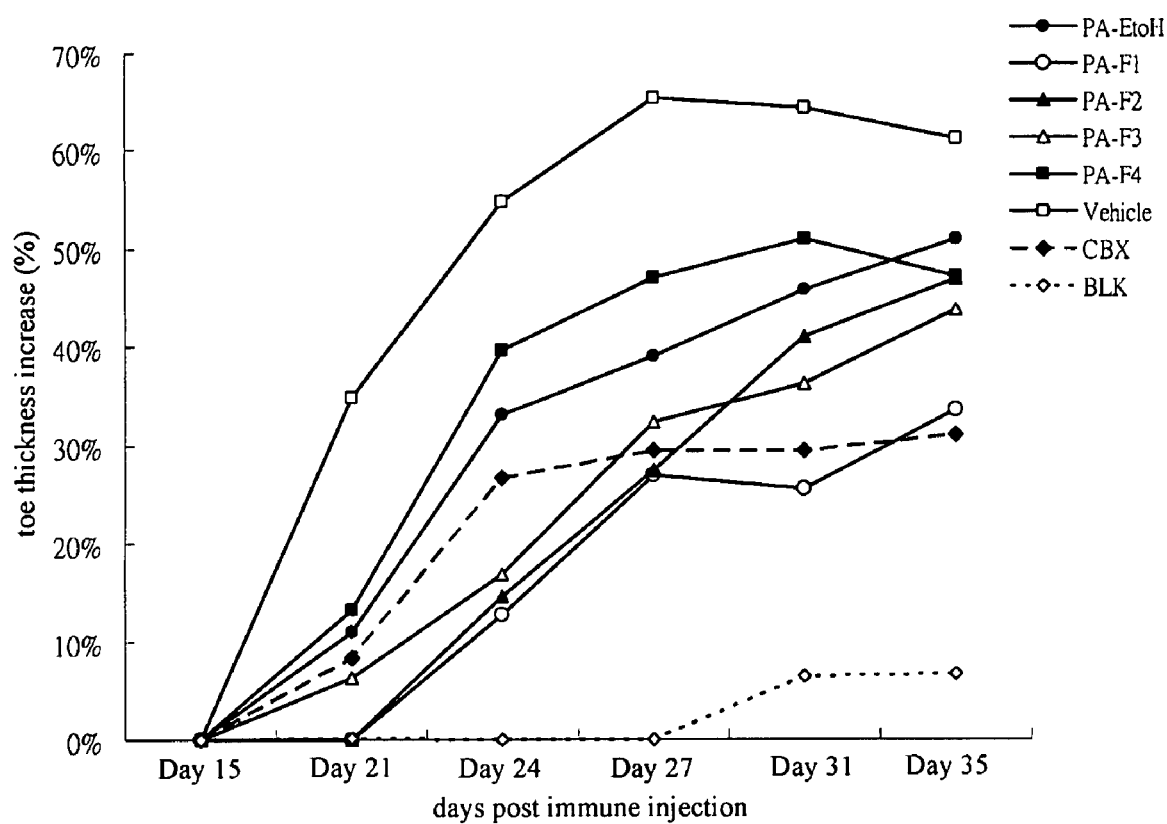
FIG. 14 illustrates the effect of feeding on PA extracts on the arthritic swelling degree of CIA rats.

Arthritis symptoms occurred successively at about Day 20 after the second immune injection of rats, and the joint sites of limbs were actually measured with a Vernier Caliper. Joint swelling rate continuously increased, and reached the highest, 64%, at Day 27. As shown in FIG. 14, it has a significant difference compared to the normal group. However, the rats fed with PA-EtOH, PA-F1, PA-F2, PA-F3, PA-F4, and CBX all exhibited the inhibiting effect of joint swelling, wherein the effect of PA-F1 and CBX is still most preferred, showing that PA-F1 may have a similar anti-inflammatory drug efficacy to that of CBX.

IV. Influence of Feeding on PA on Serum RF

Figure 15:
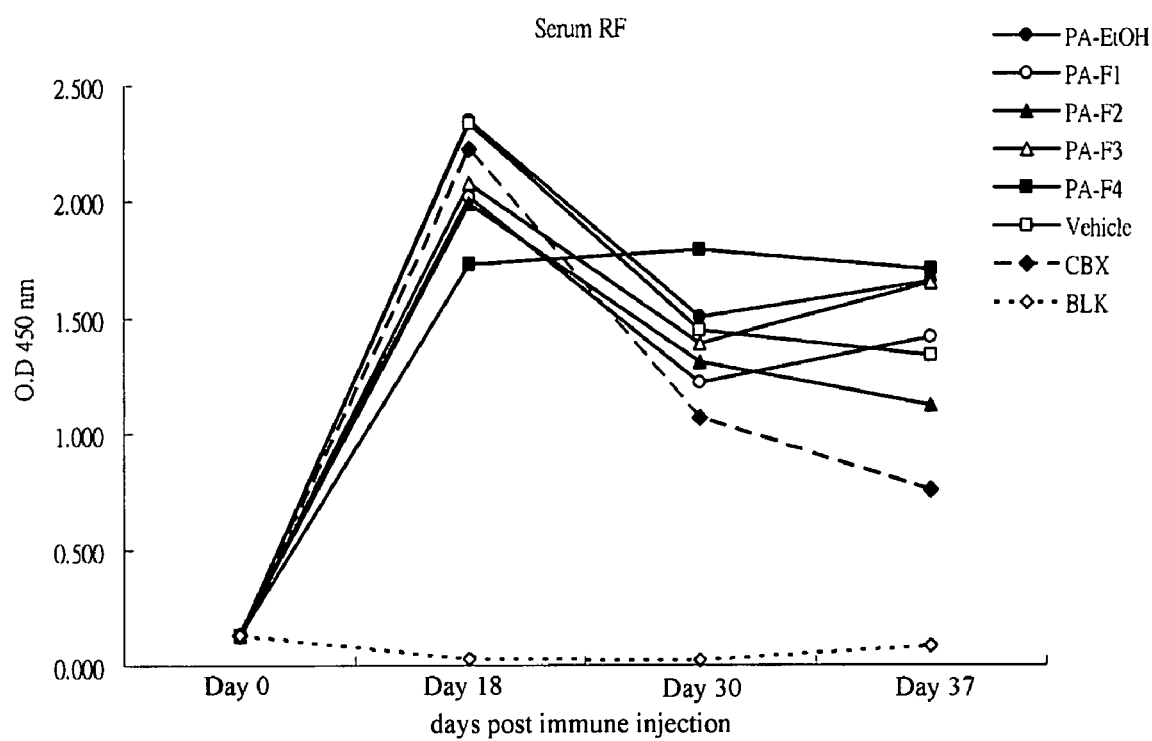
FIG. 15 illustrates the effect of feeding on PA extracts on the serum RF of CIA rats.

The analysis results show that after two immune injections, at Day 18, the serum RF titer of rats all reach the peak, as shown in FIG. 15. However, in the group feeding on PA-F2 and CBX, PA-F2 reduced RF value by about 34% at Day 30, and about 44% at Day 37, while CBX treatment reduced RF value by about 52% at Day 30, and about 66% at Day 37; and when compared to Day 18, serum RF value reduced significantly respectively.

V. Change of PEC Cytokine

Figure 16:
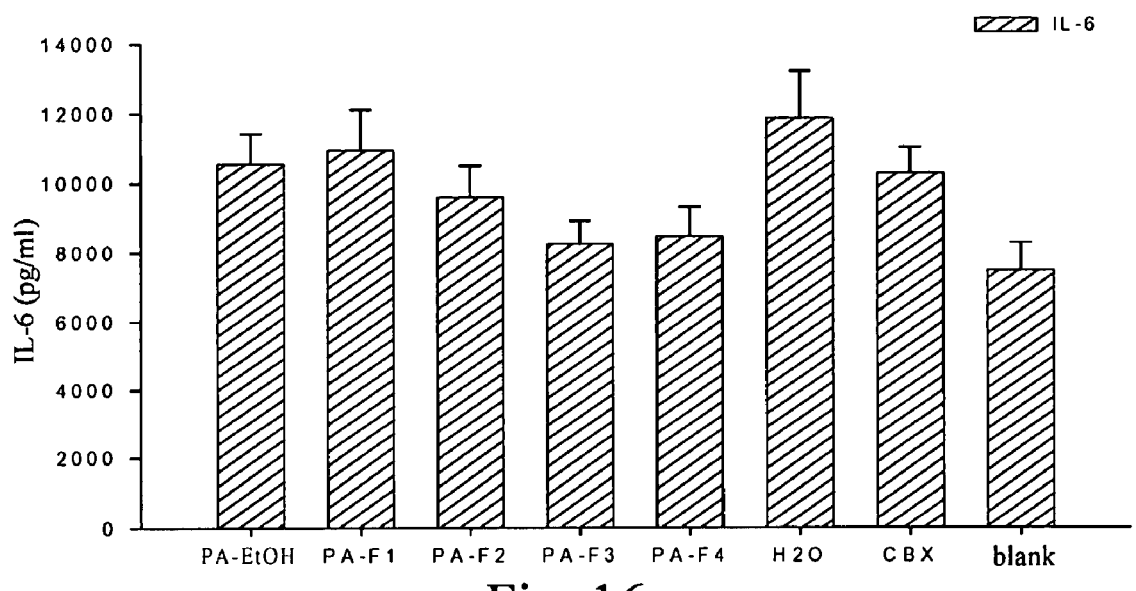
FIG. 16 illustrates the effect of feeding on PA extracts on cytokine IL-6 in the abdominal cavity of CIA rats.
Figure 17:
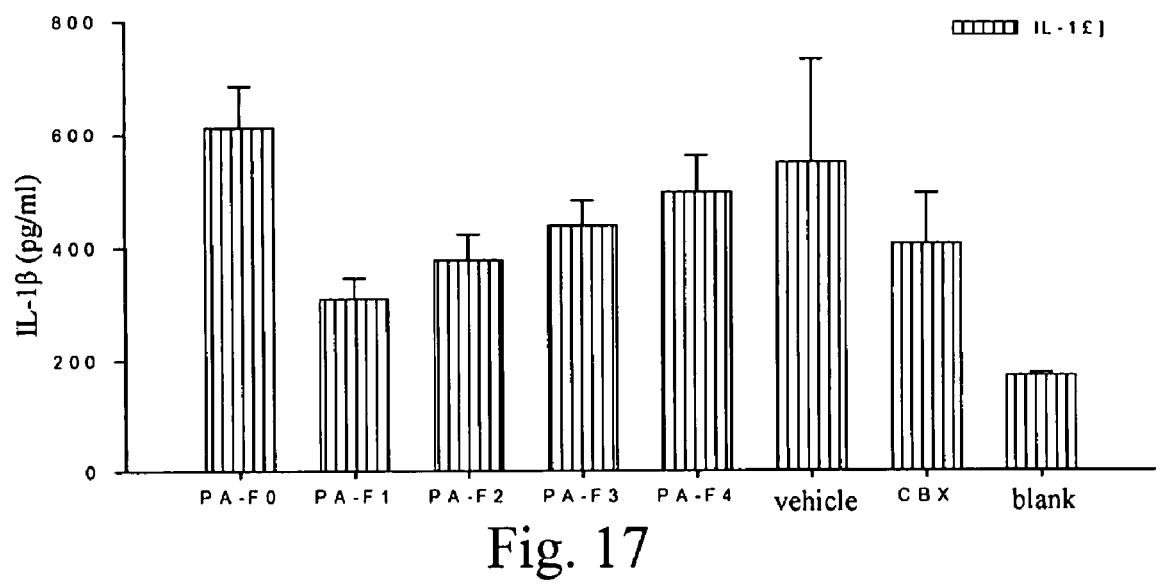
FIG. 17 illustrates the effect of feeding on PA extracts on cytokine IL-1β in the abdominal cavity of CIA rats.

The study results demonstrate that feeding PA-F2, PA-F3, and PA-F4 to CIA rats significantly inhibits PEC from secreting IL-6 (as shown in FIG. 16), and feeding PA-F1, PA-F2, and CBX to CIA rats significantly inhibits PEC from secreting IL-1β (as shown in FIG. 17).

[Conclusion]

The analysis results of the activities of the above animals are summarized in Table I:

TABLE I

|  | CBX | PA-EtOH | PA-F1 | PA-F2 | PA-F3 | PA-F4 |
|---|---|---|---|---|---|---|
| Toe thickness | ++ (49%) | + (16%) | ++ (44%) | + (23%) | + (28%) | + (23%) |
| MAI | ++ (40%) | + (34%) | ++ (46%) | + (24%) | + (37%) | + (21%) |
| RF | ++ (43%) | − (0%) | − (0%) | + (16%) | − (0%) | − (0%) |
| IL-6 | ++ (36%) | + (30%) | + (21%) | +++ (52%) | ++++ (82%) | ++++ (78%) |
| IL-1β | ++ (38%) | − (0%) | +++ (64%) | ++ (45%) | + (30%) | + (14%) |

"++++" represents 75 to 100% of inhibitory effect
"+++" represents 50 to 75% of inhibitory effect
"++" represents 25 to 50% of inhibitory effect
"+" represents 0 to 25% of inhibitory effect Embodiment 5

In Vitro Cell Model Analysis of Rat Macrophage

I. Determination Method of Concentrations of TNF-α and IL-1β

[Objective]

The concentrations of TNF-α and IL-1β in microphage RAW264.7 cell culture of rats were measured, and thereby the active ingredients capable of inhibiting LPS-induced-α synthesis were screened.

[Apparatus and Material]

1. Instrument
   (1) ELISA reader
   (2) Centrifuger
2. Assay kit DY410: Rat TNF-α/TNFSF1A (ELISA kit) (R&D, Duoset)
   (1) Carrier protein-free goat anti-rat TNF-α or IL-1β antibody: 0.8 µg/ml in phosphate buffered saline (PBS)
   (2) Biotinlated goat anti-rat TNF-α or IL-1β antibody: 150 ng/ml in diluent agent
   (3) Recombinant rat TNF-α or IL-1β in diluent agent: 2000 pg/ml
   (4) Streptavidin-HRP
3. Solutions required
   (1) PBS: 137 mM sodium chloride, 2.7 mM potassium chloride, 8.1 mM disodium hydrogen phosphate ($Na_2HPO_4$), 1.5 mM potassium dihydrogen phosphate ($KH_2PO_4$), pH 7.2~7.4
   (2) Washing buffer: 0.05% Tween 20 in PBS
   (3) Blocking buffer: 1% BSA, 5% sucrose, 0.05% sodium azide ($NaN_3$) in PBS
   (4) Diluent agent: 1% BSA in PBS
   (5) Substrate solution: Mixture of 1:1 Color Reagent A and Color Reagent B (R&D system #DY999)
   (6) Stopping solution: 2 N sulfuric acid
4. Medicaments
   (1) Griess reagent: 1% sulfanilamide and 0.1% N-(1-naphthyl)-ethylene diamine in 5% phosphoric acid
   (2) Standard: sodium nitrite
   (3) Immune stimulator: Lipopolysaccharide (LPS)
   (4) Activity control agent: nitro-L-arginine methyl ester (L-NAME), indomethacin
   (5) Culture medium: 10% fetal calf serum (FCS) in DMEM
   (6) PBS
   (7) Trypsin
5. Cell: RAW 264.7

[Method]

1. Cell culture and plating:
   (1) The old culture medium in T-75 was taken out, washed with PBS 1 to 2 times, 3 ml trypsin was added, and reacted in 37° C. for 3 minutes, after which 7 ml medium (DMEM added with 10% FCS added) was added to stop trypsin action.
   (2) It was centrifuged at 4° C. for 10 min by using a centrifuger at 1000 rpm, to remove trypsin-containing medium. 10 ml of medium was added, thoroughly mixed, and cells were counted.
   (3) RAW 264.7 cells were inoculated to a 24-well plate at a cell density of $5 \times 10^5$ cells/well, and were incubated at 37° C., in 5% carbon dioxide.
2. LPS stimulation and drug treatment
   (1) L-LAME and indomethacin (activity control agent), as well as samples were added into a phenol-free culture medium containing 1 µg/ml LPS.
   (2) The old culture medium was taken out, and changed to a fresh medium containing LPS and activity control agent or samples. This was repeated three times. They were incubated at 37° C., in 5% carbon dioxide for 18 to 24 hrs.
3. Formulation of sandwich ELISAs
   (1) 100λ of capture antibody (diluted to 0.8 µg/ml in PBS) was added to each well of a 96-well plate, and sealed at room temperature to incubate overnight.
   (2) After the removal of free capture antibody, it was washed by a washing buffer three times. 300λ of a blocking buffer was added, and incubated at room temperature for at least 1 hr to decrease non-specific binding.
   (3) Cell suspension was collected, and centrifuged at 10 krpm with a centrifuger at 4° C. for 10 min, and then stored at −20° C.

4. ELISAs analysis (1) After the removal of the blocking buffer, it was washed by the washing buffer three times. 100λ of appropriately diluted cell culture or standard (the highest concentration was 2000 pg/ml) was added, and incubated at room temperature for 2 hrs.

(2) After the removal of the cell culture or standard, it was washed by the washing buffer three times. 100λ of detecting antibody (diluted to 100 ng/ml in a solvent) was added, and incubated at room temperature for 2 hrs.

(3) After the removal of the free detecting antibody, it was washed by the washing buffer three times. 100λ of working diluted solution of Streptavidin-HRP was added, and incubated at room temperature for 20 min, avoiding light.

(4) After the removal of the free Streptavidin-HRP, it was washed by the washing buffer three times. 100λ of substrate solution was added, and incubated at room temperature for 20 min, avoiding light.

(5) 100λ of stopping solution was added and shaken gently to make it thoroughly mixed.

(6) O.D value was read out at a wavelength of 450 nm, and 540 nm or 570 nm calibration was recommended, or the read value at 570 nm (or 540 nm) was detracted directly from the read value at 450 nm.

II. NO determination

[Objective]

The concentration of nitrite (NO) in microphage RAW264.7 cell culture of rats was measured, and thereby the active ingredients capable of inhibiting LPS-induced-NO synthesis were screened.

[Apparatus and Material]

1. Instrument (1) ELISA reader (2) Centrifuger

2. Medicaments (1) Griess reagent: 1% sulfanilamide and 0.1% N-(1-naphthyl)-ethylene diamine in 5% phosphoric acid (2) Standard: sodium nitrite (3) Immune stimulator: Lipopolysaccharide (LPS)

(4) Activity control agent: nitro-L-arginine methyl ester (L-NAME), indomethacin (5) Culture medium: 10% fetal calf serum (FCS) in DMEM (6) PBS (7) Trypsin 3. Cell: RAW 264.7

[Method]

1. Cell culture and plating:

(1) The old culture medium in T-75 was taken out, washed with PBS 1 to 2 times, 3 ml trypsin was added, and reacted in 37° C. for 3 minutes, after which 7 ml medium (DMEM added with 10% FCS) was added to stop trypsin action.

(2) It was centrifuged at 4° C. for 10 min by using a centrifuger at 1000 rpm, to remove trypsin-containing medium. 10 ml of medium was added, thoroughly mixed, and cells were counted.

(3) RAW 264.7 cells were inoculated to a 24-well plate at a cell density of $5 \times 10^5$ cells/well, and were incubated at 37° C., in 5% carbon dioxide.

2. LPS stimulation and drug treatment (1) L-NAME and indomethacin (activity control agent), as well as samples were added into a phenol-free culture medium containing 1 μg/ml LPS.

(2) The old culture medium was taken out, and changed to a fresh medium containing LPS and activity control agent or samples. This was repeated three times. They were incubated at 37° C., in 5% carbon dioxide for 18 to 24 hrs.

(3) Cell suspension was collected, and centrifuged at 10 krpm with a centrifuger at 4° C. for 10 min, and then stored in −20° C.

3. Measurement of NO concentration (1) Formulation of standard: 100 μM/mL sodium nitrite (dissolved in culture medium) was formulated, and diluted 2× to obtain 7 standards in total with concentrations of 50, 25, 12.5, 6.25, 3.13, and 1.56 μM/mL respectively.

(2) The standard or the supernatant of cell culture was mixed with Griess reagent in 1:1, and incubated for 15 min under room temperature, avoiding light.

(3) O.D value was read out at a wavelength of 550 nm.

III. Determination of prostaglandin E2 ($PGE_2$)

RAW 264.7 cells were inoculated to a 24-well plate at a cell density of $10^5$ cells/well, and were incubated overnight (16 to 24 hrs). An activity control agent and test samples were added to the phenol-free culture medium containing 1 μg/ml of LPS respectively. After the removal of the old medium, 1 ml of fresh medium containing test sample and LPS was added to co-incubate. After 24 hrs, they were centrifuged at 1000 rpm with a centrifuger for 10 min. Supernatant was sucked out, and stored at −20° C., or $PGE_2$ content in the supernatant was directly quantified by using $PGE_2$ Correlate-EIA kit (Amersham RPN222).

[Conclusion]

The analysis results of the above cell models are summarized in Table II:

TABLE II

|  | PAW | PA-F1 | PA-F2 | PA-F3 | PA-F4 |
|---|---|---|---|---|---|
| NO | — | $IC_{50} > 4.27$ μg/ml | — | — | — |
| $PGE_2$ | $ED_{50} \approx 50$ μg/ml | — | $ED_{50} \approx 13.27$ μl/ml | $ED_{50} \approx 0.0423$ μg/ml | $ED_{50} \approx 185$ μg/ml |
| TNF-α | $ED_{50} > 50$ μg/ml | $ED_{50} \approx 4.27$ μg/ml | — | $ED_{50} \approx 42.3$ μg/ml | $ED_{50} > 1000$ μg/ml |
| IL-1β | $ED_{50} \approx 0.5-50$ μg/ml | — | $ED_{50} \approx 0.1327$ μg/ml | $ED_{50} \approx 4.23$ μg/ml | $ED_{50} \approx 18.5$ μg/ml |

PA extracts can inhibit rat macrophage inflammation induced by LPS. PA-F1 can significantly inhibit TNF-α produced by reddish swelling inflammatory cells induced from LPS, and PA-F2 can inhibit the effects generated by IL-1β, whereas PA-F3 can inhibit $PGE_2$, which is a product of COX.

As described above, the PA crude extract or extract used in the invention is obtained by direct juice pressing or by column separation, and it is a very safe herb that could be used externally or orally. In addition, it is demonstrated in the invention by RA rat model that when orally administrated, the PA crude extract or extract can effectively inhibit animal disorders of autoimmune diseases and related biochemical caused by collagen plus immune adjuvant, and therefore, the PA crude extract or extract has a potential anti-swelling or anti-inflammatory efficiency, and could be effectively used to treat RA.

We claim:

1. A method for treating rheumatoid arthritis in a subject in need thereof, which comprises administering a therapeutically effective amount of an extract of *Plectranthus Amboinicus* (Lour.) Spreng (PA) to the subject.

2. The method as claimed in claim 1, wherein the extract is administered in a form selected from the group consisting of capsule, tablet, powder, ointment, liquor, and spray.

3. The method as claimed in claim 1, wherein the extract is an extract obtained by direct juice pressing of PA.

* * * * *